United States Patent [19]

Diebold

[11] Patent Number: 4,650,588

[45] Date of Patent: Mar. 17, 1987

[54] SURFACE TENSION DETECTOR FOR LIQUID CHROMATOGRAPHY

[75] Inventor: Gerald J. Diebold, Barrington, R.I.

[73] Assignee: Detection Research, Inc., Barrington, R.I.

[21] Appl. No.: 745,571

[22] Filed: Jun. 17, 1985

[51] Int. Cl.$^4$ .................................. B01D 15/08
[52] U.S. Cl. .................................. 210/656; 73/58; 73/61.1 C; 422/70; 210/198.2
[58] Field of Search .............. 210/198.2, 656; 422/69, 422/70, 55, 56, 58; 436/161, 150, 151, 149; 73/58, 60, 61.1 C

[56] References Cited

U.S. PATENT DOCUMENTS 4,554,064  11/1985  McClintock .................... 436/161

FOREIGN PATENT DOCUMENTS 1033963  8/1983  U.S.S.R. ......................... 422/70

Primary Examiner—John Adee
Attorney, Agent, or Firm—Bromberg, Sunstein & McGregor

[57] ABSTRACT

A device for detecting changes in surface tension of eluant from a liquid chromatography column has in a preferred embodiment an arrangement for suspending a droplet of liquid eluting from a liquid chromatography column, a pair of electrodes in contact with the droplet, and a meter for measuring a quantity related to the resistance of the droplet of liquid.

A method for measuring the surface tension of a liquid includes forming a droplet of the liquid, causing the droplet to be supported by support elements, causing each of a pair of electrodes to come into contact with a different region of the droplet, and measuring a quantity related to the resistance of the droplet.

7 Claims, 6 Drawing Figures

SURFACE TENSION DETECTOR FOR LIQUID CHROMATOGRAPHY

TECHNICAL FIELD

The present invention relates generally to liquid chromatography, and particularly to measuring surface tension of chemical species as they elute from a liquid chromatography column.

BACKGROUND ART

Generally speaking, liquid chromatography is a method for separating, or purifying different chemical compounds. The compound is referred to as the analyte, and the liquid that is forced through the column is referred to as the eluant. The separation is based on the different properties possessed by the compounds, such as molecular weight, affinity for certain solid supports, ionic properties, etc.

The use of certain devices attached to a liquid chromatography column to detect various chemical species once they have been separated by the column is well known in the prior art. For example, universal detectors based on a change in the index of refraction of the eluant or change in the dielectric constant are used. More specific detectors that respond to ultraviolet absorption, fluorescence, or electrolytic properties of the analyte are also in common use.

The prior art, however, does not contain a detecting device that responds to changes in the surface tension of the eluant caused by the presence of an analyte. It is well known that the surface tension of a liquid is changed dramatically when certain compounds, which are sometimes referred to as surfactants, are dissolved in the liquid. An example is the lowering of the surface tension of water by soap. Lowering of the surface tension, in effect, allows the liquid to wet more easily a material with which it is in contact. The phenomenon of surface tension reduction resulting from change in the composition of a solvent is quite general and applies to both soluble solids and liquids that are added to a solvent. Some coupounds are notable in that they produce very sizeable changes in the surface tension.

DISCLOSURE OF THE INVENTION

The present invention provides a device for detecting changes in surface tension of an eluant as it flows from a liquid chromatography column. The present invention further provides a detector that, based on changes in the surface tension of the eluant, can ascertain the presence of certain chemical species injected onto the chromatography column. In addition, the present invention provides a detector that, based on changes in the surface tension of the eluant, can be used to determine the amount of an analyte present in an unknown sample injected onto the chromatography column. The invention also provides a monitor for processes that involve mixing, chemical reaction, biological change, etc., where liquid surface tension is of interest.

In a preferred embodiment, the present invention includes an arrangement for suspending a droplet of liquid eluting from a liquid chromatography column, a pair of electrodes in contact with the droplet, and a meter for measuring a quantity related to the resistance of the droplet of liquid.

The present invention also provides a method for measuring the surface tension of a liquid which includes forming a droplet of the liquid, causing the droplet to be supported by support elements, causing each of a pair of electrodes to come into contact with a different region of the droplet, and measuring a quantity related to the resistance of the droplet.

BRIEF DESCRIPTION OF THE DRAWINGS

The present invention will be more readily understood by consideration of the following detailed description taken with the accompanying drawings, in which.

DESCRIPTION OF SPECIFIC EMBODIMENTS

Figure 1:
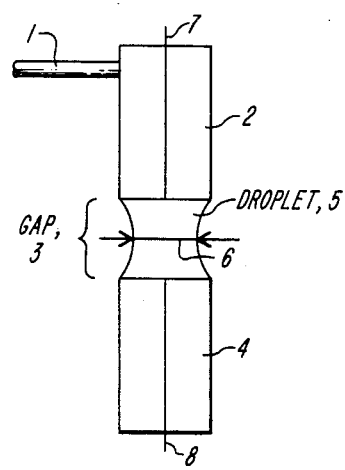
FIG. 1 is a simplified view of a preferred embodiment of the present invention, in which a droplet of eluant is suspended between two vertical, colinear, conductive supports forming electrodes, in accordance with the present invention.

Referring to FIG. 1, there is shown a preferred embodiment of the present invention. The eluant from the chromatography column, or other source, flows through tubing 1 to wet the upper support 2 of the detector. Embedded in the supports are two electrodes 7 and 8 which are used to carry a small current and hence to determine the resistance of the droplet. The gap 3 between the upper support 2 and lower support 4 is made small enough to suspend a flowing droplet 5 of eluant. If the gap is made too large, the droplet is broken and the device does not function properly. The eluant then flows downward under the force of gravity along the outer surface of the lower support where it is then collected.

The flowing liquid droplet depends on the force of surface tension to hold it in place. The exact shape of the droplet is also dependent on the magnitude of the surface tension force. If the surface tension is high, the liquid is held firmly by the upper support, and the waist 6 of the droplet is large.

Figure 2:
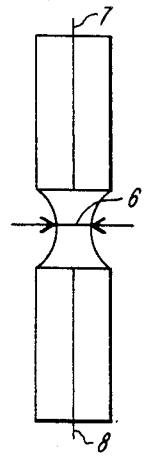
FIG. 2 is a simplified view of the embodiment in FIG. 1, wherein the surface tension of the droplet of eluant has been lowered, and the shape of the droplet has changed, in accordance with the present invention.

Turning to FIG. 2, as the surface tension is lowered, the diameter of the waist contracts.

The current through the droplet, or equivalently, its overall resistance, is determined by both the cross-sectional area of the flowing droplet and the conductivity of the eluant. Given that the conductivity of the eluant should not change appreciably in the presence of small concentrations of surfactants, the average cross-section of the droplet determines the equivalent resistance of the droplet. Thus, as different species elute from the chromatography column, the surface tension of the droplet changes, which causes the waist of the droplet to decrease (or increase), which, in turn, causes an increase (or decrease) of the equivalent resistance of the droplet. Measurement of the resistance of the droplet thus becomes a measure of the surface tension of the eluant, which varies with analyte concentration.

Figure 3:
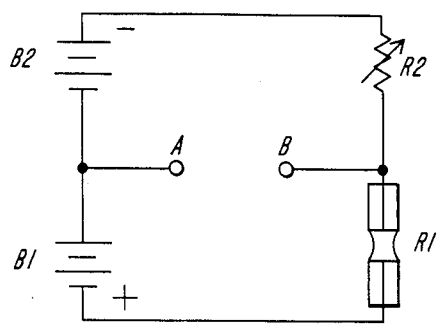
FIG. 3 is a simplified schematic of a preferred embodiment of an electrode assembly in accordance with the present invention.

Referring now to FIG. 3, there is shown a simplified schematic of an embodiment of an electrical circuit in accordance with the present invention. Batteries B1 and B2 supply a voltage for the circuit. The resistance of the eluant is shown as R1. A variable resistance R2 is connected in the circuit and can be adjusted to equal R1 when no analyte is present in the eluant. Thus, for different conductances of the eluant, or different settings of the gap length, R2 can be adjusted so that the voltage across the points A and B in the circuit is approximately zero when no analyte is present in the eluant. When an analyte that changes the surface tension of the eluant passes through the gap, the change in resistance of R1 causes a voltage to be developed across the terminals A and B. This voltage can be amplified and displayed as a function of time, or simply displayed if the recording device is sensitive enough. Note that the batteries that supply the voltage to the electrodes can be replaced by a suitable power supply. In this arrangement the tubing 1 (shown in FIG. 1) that brings the eluant to the detector is non-conducting so that very little current can flow back to the chromatography column or pump.

Figure 4:
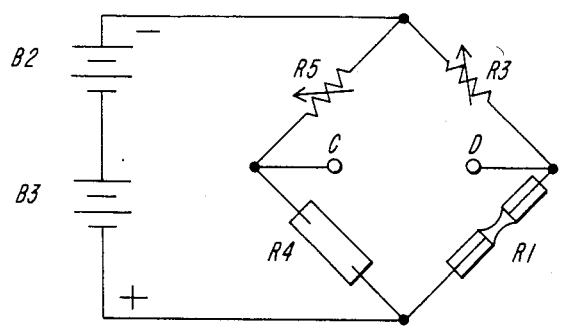
FIG. 4 is a simplified schematic of a preferred embodiment of an electrical bridge circuit that employs conductivity compensation in accordance with the present invention.

Turning now to FIG. 4, there is shown a bridge circuit employing conductivity compensation. The resistance of the liquid droplet is again given by R1. The compensation cell has a resistance R4 which is approximately the same value as R1. The variable resistors R3 and R5 form the remainder of the bridge. The bridge uses batteries B3 and B4, which can be grounded at their connection, to provide the bias current. In practice, the voltage across the output terminals C and D is set to zero by adjusting R3 and R5. The compensation cell provides a method for cancelling out the effects of a changing conductivity of the eluant, which can be caused by temperature variations, gradient elution, improper mixing of the solvents, or other factors. As the eluant conductivity changes, the increase, or decrease, in voltage across R1 is matched by a similar increase, or decrease, in voltage across R4. Thus, conductivity changes appear as a simultaneous, or common-mode, increase in potential at both C and D. Since the recording device is assumed to respond only to the voltage difference between points C and D in the circuit, thus rejecting common-mode signals, the change in eluant conductivity is eliminated.

Figure 5:
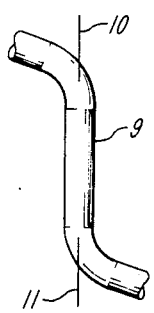
FIG. 5 is a simplified view of an embodiment of the compensation cell used in conjunction with the compensation circuit shown in FIG. 4 in accordance with the present invention, wherein two electrodes are embedded in a short section of non-conducting tubing through which the eluant flows.

Referring now to FIG. 5, there is shown a simplified view of an embodiment of of the compensation cell in FIG. 4. The cell is simply a short section of non-conducting tubing 9 through which the eluant flows. Two electrodes 10 and 11 are embedded in the cell so that a small current can be passed through the cell.

Figure 6:
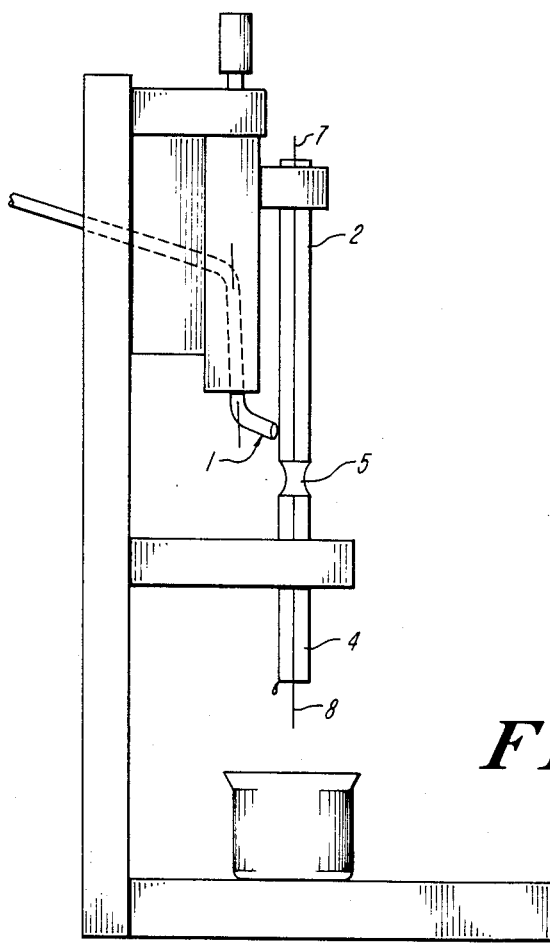
FIG. 6 is a simplified view of a preferred embodiment of the present invention, wherein the electrode assembly is adjusted by a micrometer screw in accordance with the present invention.

Turning now to FIG. 6, there is shown a more complete view of a preferred embodiment of the present invention. The supports for the droplet are mounted so that the lower support 4 is fixed and the upper support 2 is moveable. This permits the accurate setting of the gap distance so that the sensitivity of the detector can be maximized. The eluant from the chromatography column flows onto the upper support 2, enters the gap, and flows to the lower support 4, where it drips off, or is otherwise collected. The supports are mounted on insulated blocks to prevent an unwanted flow of current back to the base of the instrument.

What is claimed is:
1. A device, for the measurement of the surface tension of a liquid eluting from a liquid chromatography column, the device comprising:
   (a) input means for receiving liquid from a liquid chromatography column and forming a droplet of the liquid;
   (b) support means in communication with the input means for suspending a droplet of the liquid;
   (c) a first pair of electrodes, each of which is in contact with a different region of a droplet suspended by the support means, so that the volume of fluid electrically connecting the two electrodes varies with the surface tension of the fluid, resulting in the resistance between the two electrodes also varying with the surface tension of the fluid;
   (d) metering means, connected in a circuit with the electrodes, for measuring a quantity related to the resistance of the droplet, such that changes in the surface tension of the liquid are thereby monitored; and
   (e) compensation cell means through which the liquid flows and having a second pair of electrodes connected to the circuit for cancelling out the effects of changes in conductivity of the liquid per unit volume.

2. A device according to claim 1, wherein the support means and the electrodes collectively include support elements so disposed in relation to each other so as to define a gap between them of a size permitting the suspension of the droplet.

3. A device according to claim 2, wherein each of the support elements is conductive, is vertically disposed, and forms an electrode.

4. A device according to claim 3, wherein the support elements are colinear.

5. A method, for measuring the surface tension of liquid, the method comprising:
   (a) forming a droplet of the liquid;
   (b) causing the droplet to be suspended by two support elements so disposed in relation to each other as to define a gap between them of a size permitting the suspension of the droplet;
   (c) causing each of a pair of electrodes to come in contact with a different region of the droplet; and
   (d) measuring a quantity relating to the resistance of the droplet.

6. A method according to claim 5, further comprising the step of using as the source of the liquid the eluant exiting a liquid chromatography column.

7. A device, for the measurement of the surface tension of a liquid eluting from a liquid chromatography column, the device comprising:
   (a) input means for receiving liquid from a liquid chromatography column and forming a droplet of the liquid;
   (b) support means in communication with the input means for suspending a droplet of the liquid;
   (c) a pair of electrodes, each of which is in contact with a different region of a droplet suspended by the support means, so that the volume of fluid electrically connecting the two electrodes varies with the surface tension of the fluid, resulting in the resitance between the two electrodes also varying with the surface tension of the fluid; and
   (d) metering means, connected in a circuit with the electrodes, for measuring a quantity related to the resistance of the droplet, such that changes in the surface tension of the liquid are thereby monitored.

* * * * *